(12) United States Patent
Reddy et al.

(10) Patent No.: US 10,239,836 B2
(45) Date of Patent: Mar. 26, 2019

(54) BENZENECARBOTHIOCCYCLOPENTA[C] PYRROLE-1,3-DIONE COMPOUNDS AND PROCESS FOR SYNTHESIS THEREOF

(71) Applicant: Council of Scientific & Industrial Research, New Delhi (IN)

(72) Inventors: Dumbala S. Reddy, Pune (IN); Satish C. Philkhana, Pune (IN); Gorakhnath R. Jachak, Pune (IN); Vidya B. Gunjal, Pune (IN)

(73) Assignee: Council of Scientific & Industrial Research, New Delhi (IN)

( * ) Notice: Subject to any disclaimer, the term of this patent is extended or adjusted under 35 U.S.C. 154(b) by 0 days.

(21) Appl. No.: 15/515,487

(22) PCT Filed: Oct. 1, 2015

(86) PCT No.: PCT/IN2015/050126
§ 371 (c)(1),
(2) Date: Mar. 29, 2017

(87) PCT Pub. No.: WO2016/051425
PCT Pub. Date: Apr. 7, 2016

(65) Prior Publication Data
US 2017/0226057 A1 Aug. 10, 2017

(30) Foreign Application Priority Data

Oct. 1, 2014 (IN) .............. 2815/DEL/2014
Oct. 1, 2014 (IN) .............. 2816/DEL/2014

(51) Int. Cl.
*C07D 209/52* (2006.01)
*C07D 409/12* (2006.01)

(52) U.S. Cl.
CPC ......... *C07D 209/52* (2013.01); *C07D 409/12* (2013.01)

(58) Field of Classification Search
CPC .............................. C07D 209/52; C07D 409/12
See application file for complete search history.

(56) References Cited

U.S. PATENT DOCUMENTS 6,353,112 B1 * 3/2002 Baker .................. C07D 275/06
548/207
2009/0092624 A1 4/2009 Alberte et al.

OTHER PUBLICATIONS

Dorwald, F. Zaragoza. Side Reactions in Organic Synthesis: A Guide to Successful Synthesis Design, Weinheim: Wiley-VCH Verlag GmbH & Co. KGaA, 2005, Preface (Year: 2005).*
Merriam-Webster entry for "derivative" (Obtained from http://www.merriam-webster.com/dictionary/derivative on Aug. 5, 2014 (Year: 2014).*
Merriam-Webster Online Dictionary entry for "analogue", (http://www.merriam-webster.com/dictionary/analogue), last accessed May 12, 2010 (Year: 2010).*
A. Yang et al., "Nitrosporeusines A and B, Unprecedented Thioester-Bearing Alkaloids from the Arctic Streptomyces Nitrosporeus," Organic Letters vol. 15, No. 20, 5366-5369, (2013).
S. C. Philkhana et al., "First synthesis of nitrosporeusines, alkaloids with multiple biological activities," Tetrahedron Letters 56, 1252-1254, (2015).
International Search Report and Written Opinion issued in PCT/IN2015/050126, dated Jan. 4, 2016.

* cited by examiner

*Primary Examiner* — Matthew P Coughlin
(74) *Attorney, Agent, or Firm* — Locke Lord LLP; Nicholas J. DiCeglie, Jr.

(57) ABSTRACT

The present invention relates to a novel analogs of benzenecarbothioccyclopenta[c]pyrrole-1,3-dione of formula (I) useful for treating various viral infections and process for synthesis thereof.

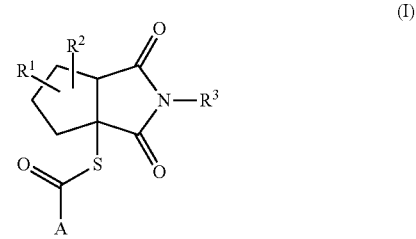

(I)

The present invention provides a novel process for synthesis of nitrosporeusines A(1) and B(2). More particularly, the present invention provides a synthetic route for synthesis of nitrosporeusines A(1) and B(2). Said process is simple, industrially scalable, cost effective and eco-friendly.

8 Claims, 5 Drawing Sheets nitrosporeusine B (-) 2 nitrosporeusine A (+) 1 nitrosporeusine B (+) 2 nitrosporeusine A (-) 1

BENZENECARBOTHIOCCYCLOPENTA[C] PYRROLE-1,3-DIONE COMPOUNDS AND PROCESS FOR SYNTHESIS THEREOF

CROSS REFERENCE TO RELATED APPLICATIONS

This application is a 371 U.S. National Phase Application of PCT/IN2015/050126, filed Oct. 1, 2015, which claims priority to Indian Patent Application No. 2815/DEL/2014, filed Oct. 1, 2014 and Indian Patent Application No. 2816/DEL/2014, filed Oct. 1, 2014.

FIELD OF THE INVENTION

The present invention relates to benzenecarbothioccyclopenta[c]pyrrole-1,3-dione compound of formula (I) and process for synthesis thereof. Particularly the present invention relates to a process for synthesis of Nitrosporeusines A and B useful as antivirals or anti-inflammatory agents.

BACKGROUND OF THE INVENTION

One of the dreadful disease rapidly spreading across the globe in epidemics is influenza commonly referred to as "flu". It is an infectious disease caused by RNA viruses of the family Orthomyxoviridae known as the influenza viruses. Influenza spreads around the world in seasonal epidemics, resulting in about three to five million yearly cases of severe illness and about 250,000 to 500,000 yearly deaths, rising to millions in some pandemic years. The current existing drugs in market to treat influenza viruses are increasingly becoming ineffective due to constant resistance being developed by viruses and discovery on new inhibitors with novel mode of action is necessary.

The need for discovery of new inhibitors gains much attention by the research community and accordingly ample research on synthesis of novel anti-viral compounds has been reported. The parallel research in natural products has also been reported for the identification of novel anti-viral compounds so as to overcome the menace of drug resistance. One such natural product family with good inhibitory activities against the H1N1 virus is Nitrosporeusine.

Article titled "Nitrosporeusines A and B, Unprecedented Thioester-Bearing Alkaloids from the Arctic *Streptomyces nitrosporeus*" by Aigang Yang et al. published in Organic Letter, 2013, 15 (20), pp 5366-5369 reports chemical examination of an arctic actinomycete *Streptomyces nitrosporeus* resulted in the isolation of two alkaloids named as Nitrosporeusine A and Nitrosporeusine B with an unprecedented skeleton containing benzenecarbothioccyclopenta[c]pyrrole-1,3-dione. Both Nitrosporeusine exhibited inhibitory activities against the H1N1 virus in MDCK cells.

Chinese Pat. No. 103599102 discloses a novel use of a compound Nitrosporeusines A, particularly concerning Nitrosporeusines A in the manufacture of a medicament for the treatment of acute renal failure in the application.

Chinese Pat. No. 103585147 discloses application of Nitrosporeusines A in preparation of oral ulcer treatment or prevention medicines.

Chinese Pat. No. 103585150 discloses use of Nitrosporeusines A in preparation of drugs for treating immune-inflammation and especially for treating rhinitis.

Chinese Pat. No. 103585149 discloses application of Nitrosporeusines A in medicines for treating and preventing renal fibrosis.

Chinese Pat. No. 103585148 discloses use of Nitrosporeusines A in the preparation of chronic heart failure treatment or prevention medicines.

Therefore, there is a need to come up with newer compounds with better and newer activities to successfully curtail the danger of increased drug resistance as well as to improve the life span of a subject suffering such illnesses.

OBJECTIVE OF THE INVENTION

The main objective of the present invention is to provide benzenecarbothioccyclopenta[c]pyrrole-1,3-dione compound of formula (I).

Another objective of the present invention is to provide a process for synthesis of compound of formula (I).

Another objective of the present invention is to provide a synthetic route for synthesis of nitrosporeusines A and B.

Still another objective of the present invention is to provide a simple and industrially scalable process for synthesis of nitrosporeusines A and B.

Yet another objective of the present invention is to provide cost effective process for synthesis of nitrosporeusines A and B.

BRIEF DESCRIPTION OF ACCOMPANYING DRAWINGS

SUMMARY OF THE INVENTION

Figure 1:
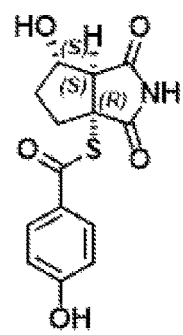
FIG. 1 represents stereoisomers of Nitrosporeusines A (1) and B(2).
Figure 1:
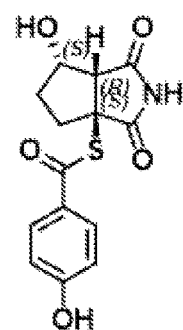
Figure 1:
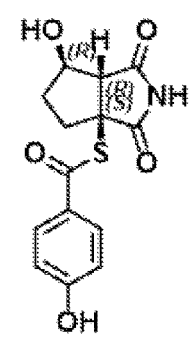
Figure 1:
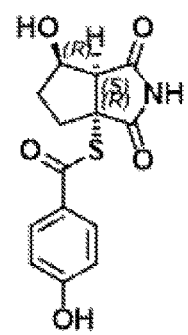

The present invention provides benzenecarbothioccyclopenta[c]pyrrole-1,3-dione compound of formula (I) and process for synthesis thereof which are expected to show better activities against influenza viruses than the existing drugs. Further, the various compounds prepared based on this novel scaffold are expected to show good inhibitory activity not only against influenza viruses but also for treatment of acute renal failure, rhinitis, renal fibrosis and chronic heart failure.

DETAILED DESCRIPTION OF THE INVENTION

Accordingly, present invention provides benzenecarbothioccyclopenta[c]pyrrole-1,3-dione compound of formula (I).

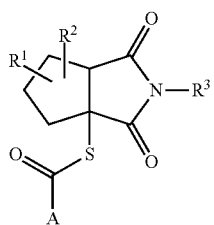

Formula I wherein,

R¹ and R² are individually selected from hydrogen, alkyl, alkenyl, aryl, heteroaryl, hydroxyl, alkoxy, heteroaryloxy, carboxy, alkylcarbonyl, arylcarbonyl, alkoxycarbonyl, cyano, halo, azide, thioocyano, alkylcarbothioc or arylcarbothioc; or R1 and R2 may form a 3 to 8 membered carbocyclic ring which may optionally be substituted or may contain a 1-2 heteroatoms;

R³ is selected from hydrogen, alkyl, alkenyl, alkynyl, cycloalkyl, cylcoalkenyl, aryl, heteroaryl, hydroxyl, alkoxy, heteroaryloxy, alkylcarbonyl, arylcarbonyl, or alkoxycarbonyl; and A is selected from alkyl, alkenyl, alkynyl, cycloalkyl, cylcoalkenyl, aryl, heteroaryl, hydroxyl, alkoxy or aryloxy.

provided that when R² and R³ are Hydrogen, R¹ is not OH and A is not aryloxy and its derivatives, salts, analogues and isomers.

Accordingly, the present invention encompasses the following exemplary compounds of formula I.

a) S-((3aR,6R,6aS)-6-hydroxy-1,3-dioxohexahydrocyclopenta[c]pyrrol-3a(1H)-yl) 4-hydroxybenzothioate (−)1;
b) S-((3aS,6R,6aR)-6-hydroxy-1,3-dioxohexahydrocyclopenta[c]pyrrol-3a(1H)-yl) 4-hydroxybenzothioate (+)2;
c) S-((3aS,6S,6aR)-6-hydroxy-1,3-dioxohexahydrocyclopenta[c]pyrrol-3a(1H)-yl) 4-hydroxybenzothioate ((+)1);
d) S-((3aR,6S,6aS)-6-hydroxy-1,3-dioxohexahydrocyclopenta[c]pyrrol-3a(1H)-yl) 4-hydroxybenzothioate ((−)2);
e) S-(3aR*,6R*,6aS*)-6-Hydroxy-1,3-dioxohexahydrocyclopenta[c]pyrrol-3a(1H)-yl) ethanethioate (7);
f) S-(3aS*,6R*,6aR*)-6-Hydroxy-1,3-dioxohexahydrocyclopenta[c]pyrrol-3a(1H)-yl) ethanethioate (8);
g) S-(3aR*,6R*,6aS*)-6-Hydroxy-1,3-dioxohexahydrocyclopenta[c]pyrrol-3a(1H)-yl) 2-phenylethanethioate (9);
h) S-(3aS*,6R*,6aR*)-6-Hydroxy-1,3-dioxohexahydrocyclopenta[c]pyrrol-3a(1H)-yl) 2-phenylethanethioate (10);
i) S-(3aS*,6R*,6aR*)-6-Hydroxy-1,3-dioxohexahydrocyclopenta[c]pyrrol-3a(1H)-yl) 4-fluorobenzothioate (11)
j) S-(3aS*,6R*,6aR*)-6-Hydroxy-1,3-dioxohexahydrocyclopenta[c]pyrrol-3a(1H)-yl)thiophene-2-carbothioate (12)
k) S-((3aS*,6S*,6aR*)-6-Hydroxy-1,3-dioxohexahydrocyclopenta[c]pyrrol-3a(1H)-yl) 2-chlorobenzothioate (13);
l) S-(3aS*,6R*,6aR*)-6-Hydroxy-1,3-dioxohexahydrocyclopenta[c]pyrrol-3a(1H)-yl) 2-chlorobenzothioate (14);
m) S-((3aR*,6R*,6aS*)-6-Hydroxy-1,3-dioxohexahydrocyclopenta[c]pyrrol-3a(1H)-yl) benzothioate (15);
n) S-(3aS*,6R*,6aR*)-6-Hydroxy-1,3-dioxohexahydrocyclopenta[c]pyrrol-3a(1H)-yl) benzothioate (16);
o) S-(3aS*,6R*,6aR*)-6-Hydroxy-1,3-dioxohexahydrocyclopenta[c]pyrrol-3a(1H)-yl) 2-hydroxybenzothioate (17);
p) S-((3aR*,6aS*)-1,3-Dioxohexahydrocyclopenta[c]pyrrol-3a(1H)-yl) ethanethioate (18);
q) S-((3aR*,6aS*)-1,3-Dioxohexahydrocyclopenta[c]pyrrol-3a(1H)-yl) 2-phenylethanethioate (19);
r) S-((3aR*,6aS*)-1,3-Dioxohexahydrocyclopenta[c]pyrrol-3a(1H)-yl) 4-fluorobenzothioate (20);
s) S-((3aR*,6aS*)-1,3-Dioxohexahydrocyclopenta[c]pyrrol-3a(1H)-yl) 2-chlorobenzothioate (21);
t) S-(1,3-Dioxo-2,3,4,5-tetrahydrocyclopenta[c]pyrrol-3a(1H)-yl) 4-fluorobenzothioate (22);
u) S,S'-((3aR*,6aR*)-1,3-Dioxohexahydrocyclopenta[c]pyrrole-3a,6(1H)-diyl) bis(4-fluorobenzothioate) (23);
v) S-(1,3-Dioxo-1,2,3,4,5,6-hexahydrocyclopenta[c]pyrrol-4-yl) benzothioate (24);
w) S,S'-((3aS*,6aS*)-1,3-Dioxohexahydrocyclopenta[c]pyrrole-3a,6(1H)-diyl) dibenzothioate (25);
x) S-(1,3-Dioxo-2,3,4,5-tetrahydrocyclopenta[c]pyrrol-3a(1H)-yl)ethanethioate (26)
y) S-(1,3-Dioxo-2,3,4,5-tetrahydrocyclopenta[c]pyrrol-3a(1H)-yl) 2-phenylethanethioate (27);
z) S,S'-((3aR*,6aR*)-1,3-Dioxohexahydrocyclopenta[c]pyrrole-3a,6(1H)-diyl) diethanethioate (28);
aa) S-(1,3-Dioxo-1,2,3,4,5,6-hexahydrocyclopenta[c]pyrrol-4-yl)thiophene-2-carbothioate (29);
bb) (3aS*,6aR*)-1,3-Dioxo-6a-((thiophene-2-carbonyl) thio)octahydrocyclopenta[c]pyrrol-4-yl acetate (30);
cc) (3aS*,6aR*)-6a-(Acetylthio)-1,3-dioxooctahydrocyclopenta[c]pyrrol-4-yl acetate (31);
dd) (3aS*,6aR*)-1,3-Dioxo-6a-(2-phenylacetyl)thio)octahydrocyclopenta[c]pyrrol-4-yl acetate (32);
ee) (3aS*,6aR*)-6a-((4-Fluorobenzoyl)thio)-1,3-dioxooctahydrocyclopenta[c]pyrrol-4-yl acetate (33);
ff) (3aS*,6aR*)-6a-((2-Chlorobenzoyl)thio)-1,3-dioxooctahydrocyclopenta[c]pyrrol-4-yl acetate (34);
gg) (3aS*,6aR*)-6a-(Benzoylthio)-1,3-dioxooctahydrocyclopenta[c]pyrrol-4-yl acetate (35).

Figure 2:
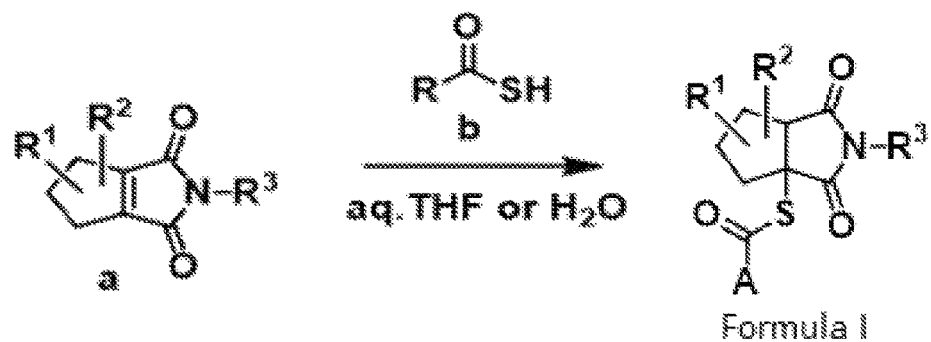
FIG. 2 represents process steps for the synthesis of compound of formula I.

In an embodiment, present invention provides a process for synthesis of compound of formula (I) comprises reacting thioacid of formula (b) with compound of formula (a) in suitable solvent followed by extraction to afford compound of formula (I). The above process is shown in FIG. 2.

In another embodiment of the present invention, the reaction mixture is stirred vigorously at a temperature ranging from 25° C. to 100° C. ambient temperature to reflux temperature of the solvent used.

In another embodiment of the present invention, the reaction mixture is stirred at room temperature for 2 to 15 hrs.

In another embodiment of the present invention, the solvent may be selected from the group consisting of hydrocarbon solvents, water, alcohols, ethers, esters, cyclic ethers and nitriles or combination thereof.

In another embodiment of the present invention, the compound of formula (a) is selected from 5,6-dihydrocyclopenta[c]pyrrole-1,3(2H,4H)-dione; 4-hydroxy-5,6-dihydrocyclopenta[c]pyrrole-1,3(2H,4H)-dione; 4-bromo-5,6-dihydrocyclopenta[c]pyrrole-1,3(2H,4H)-dione; 1,3-dioxo-1,2,3,4,5,6-hexahydrocyclopenta[c]pyrrol-4-yl acetate.

In another embodiment of the present invention, the compound of formula (b) may be selected from ethanethioic S-acid; 2-chlorobenzothioic S-acid; 4-fluorobenzothioic S-acid; benzothioic S-acid; 2-hydroxybenzothioic S-acid;

4-hydroxybenzothioic S-acid; thiophene-2-carbothioic S-acid; 2-phenylethanethioic S-acid.

In another embodiment of the present invention, the present invention provides a process for synthesis of nitrosporeusines A (1) and B (2) comprising the steps of:

a) adding oxidizing agent to a solution of 5, 6-dihydroclopenta[c]pyrrole-1, 3 (2H, 4H)-dione (3) at a temperature 25° C. in dry solvent;

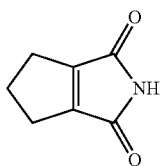

3 b) subjecting reaction mixture of step (a) to microwave irradiation to afford 4-hydroxy-5,6-dihydroclopenta[c]pyrrole-1, 3 (2H, 4H)-dione (4);

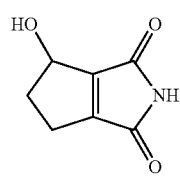

4 c) reacting 4-hydroxy-5,6-dihydroclopenta[c]pyrrole-1, 3 (2H, 4H)-dione (4) of step (b) with thiobenzoic acid in presence of water to afford mixture of Nitrosporeusines A (1) & B(2).

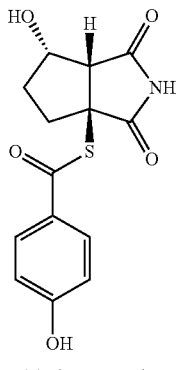
(±) nitrosporeusine A, 1

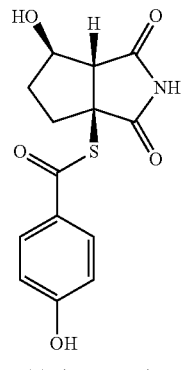
(±) nitrosporeusine B, 2

Figure 3:
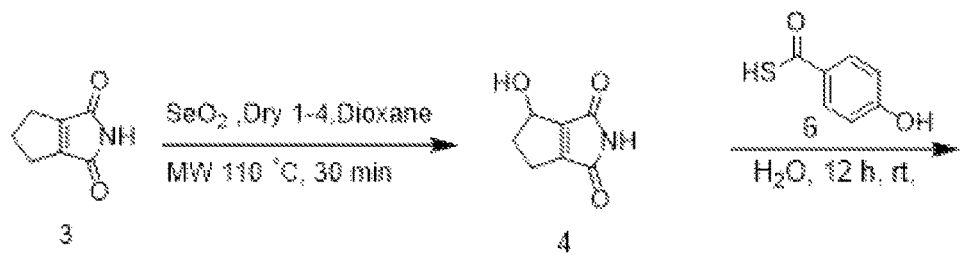
FIG. 3 represents process steps for the synthesis of Nitrosporeusine A (1) and B(2).
Figure 3:
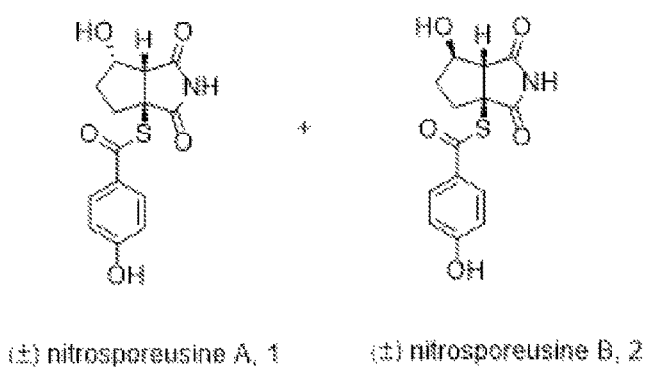
Figure 4:
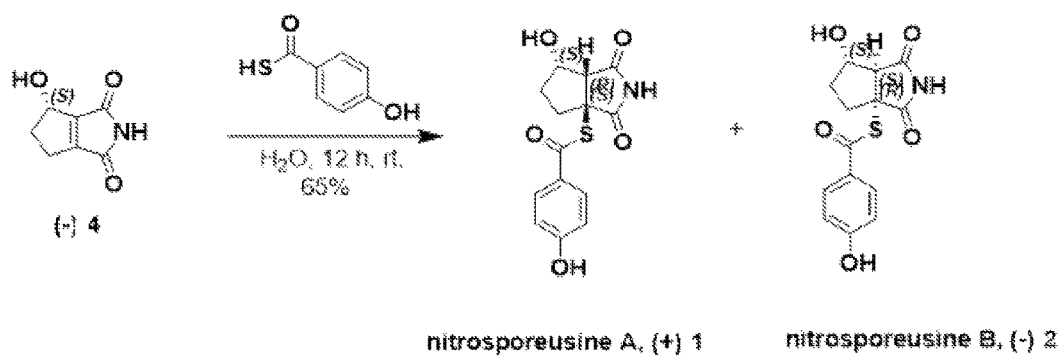
FIG. 4 represents process steps for the synthesis of Nitrosporeusines A (+)1 and B(−)2.
Figure 5:
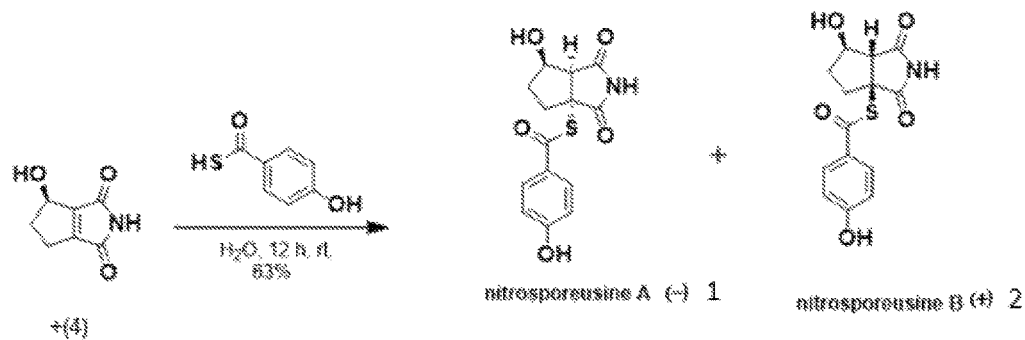
FIG. 5 represents process steps for the synthesis of Nitrosporeusines A (−)1 and B(+)2.
Figure 6:
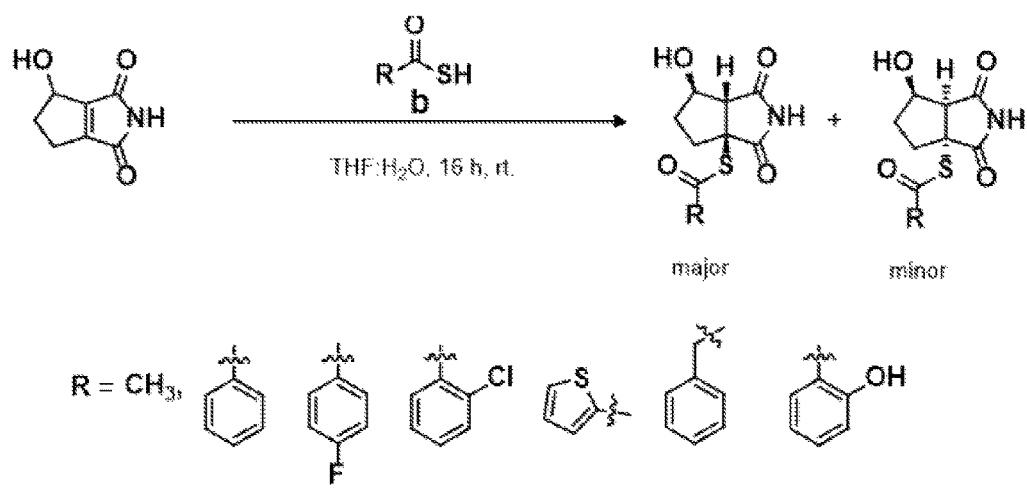
FIG. 6 represents general outline for Synthesis of compounds 7 to 17, wherein the average yield of the reactions is 70-80% combined yield of both diastereomers.
Figure 7:
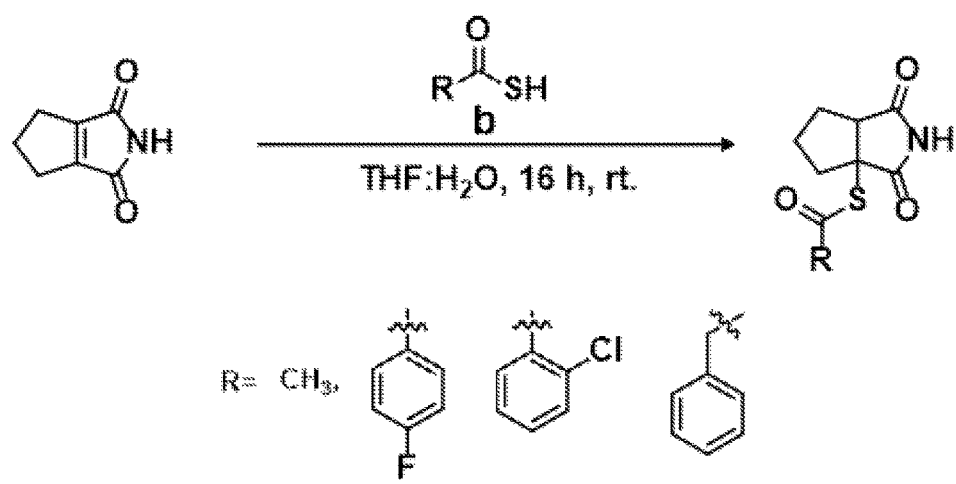
FIG. 7 represents general outline for synthesis of compounds 18 to 21, wherein the average yield of the reactions is 40-70%.
Figure 8:
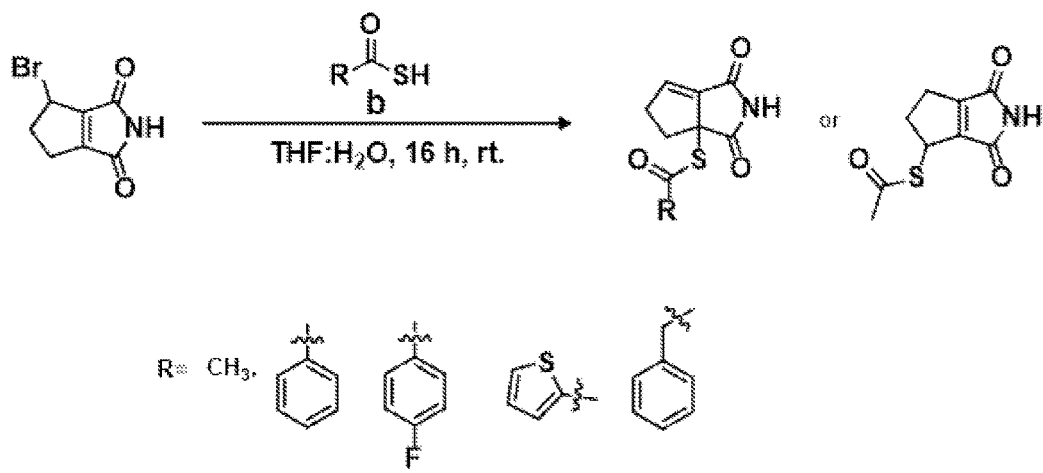
FIG. 8 represents general outline for synthesis of compounds 22 to 29, wherein the average yield of the reactions is 40-50%.
Figure 9:
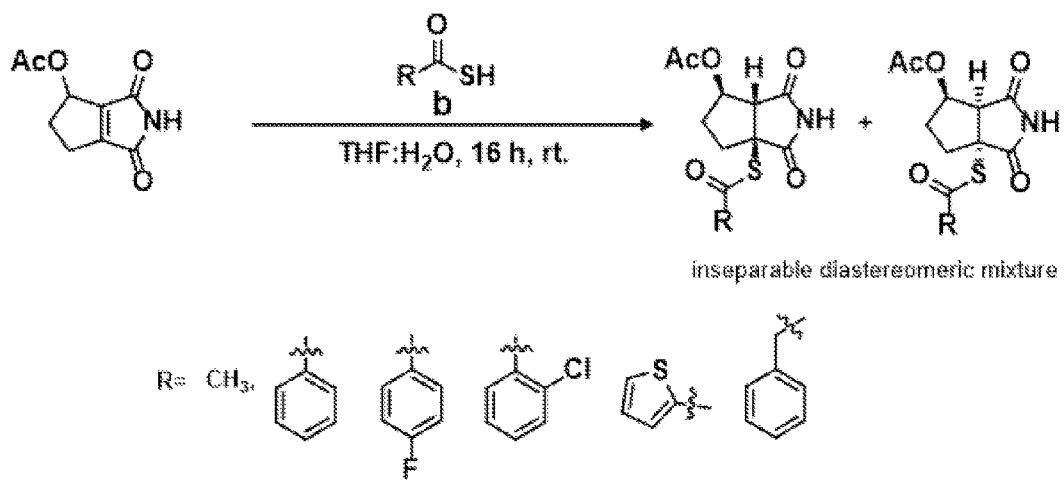
FIG. 9 represents general outline for synthesis of compounds 30 to 35, wherein the average yield of the reactions is 50-65% and all the acetates compounds are isolated as inseparable diastereomeric mixtures (~3:7).

The above process is shown in FIG. 3.

In another embodiment of the present invention, the microwave irradiation of reaction mixture of step (b) may be carried out at a temperature ranging from 100° C. to 150° C., preferably at 110° C. for 30 min to 1 hr to afford said compound (4). Said compound (4) is isolated by evaporation of solvent and purified by chromatographic methods.

In another embodiment of the present invention, the step (c) may be carried out at a temperature ranging from ambient temperature to reflux temperature of the solvent. Preferably the reaction may be carried out at a temperature ranging from 30° C. to 100° C. The reaction may be continued for a period of 10 to 24 hrs by monitoring the progress of the reaction. Once the reaction is completed, the reaction mixture is extracted with suitable organic solvent to isolate the Nitrosporeusines A (1) & B (2) as a mixture, which can be separated by subjecting the mixture to column chromatography.

In another embodiment of the present invention, the oxidizing agent is selected from Selenium dioxide ($SeO_2$).

In another embodiment of the present invention, the solvent is selected from 1,4-dioxane, tetrahydrofuran, ethanol, methanol and like.

In another embodiment of the present invention, the thiobenzoic acid used is 4-hydroxybenzothioic S-acid.

In another embodiment, present invention provides a pharmaceutical composition comprising a compound of formula (I), or a stereoisomer, or ester or pharmaceutically acceptable salt thereof, and a pharmaceutically acceptable carrier, diluent or excipient.

The synthesized compounds are analogues of parent compounds nitrosporeusines A and B which are known to possess anti-viral activities, especially against H1N1 influenza virus. The anti-inflamatory activity is being analysed with respect to Nitrogen oxide inhibition The pharmaceutical compositions of the invention can be prepared by combining a compound of the invention with an appropriate pharmaceutically acceptable carrier, diluent or excipient, and may be formulated into preparations in solid, semi-solid, liquid or gaseous forms, such as tablets, capsules, powders, granules, ointments, solutions, injections, gels and microspheres, The present invention relates to administering 'an effective amount' of the 'composition of invention' to the subject suffering from said disease. Accordingly, compound of formula I and pharmaceutical compositions containing them may be administered using any amount, any form of pharmaceutical composition via any route of administration effective for treating the disease. Typical routes of administering such pharmaceutical compositions include, without limitation, oral, topical, transdermal, inhalation, parenteral, sublingual, buccal, rectal, vaginal, and intranasal.

Pharmaceutical compositions of the invention are formulated so as to allow the active ingredients contained therein to be bioavailable upon administration of the composition to a patient. Compositions that will be administered to a subject or patient may take the form of one or more dosage units. The dosage forms can also be prepared as sustained, controlled, modified and immediate dosage forms.

EXAMPLES

Following examples are given by way of illustration and therefore should not be construed to limit the scope of the invention.

General Example

Synthesis of Compound of formula I through Michael Addition Reaction

In a round-bottomed flask equipped with a magnetic stirrer, thioacid (b) (1.1 eq.), substituted imide (a) (1 eq.), and THF:water (1:1, 2 mL) were charged. The reaction mixture was stirred vigorously at room temperature for 2 to 15 h, then it was diluted with ethyl acetate and extracted twice (2×3 ml). The combined organic layer was washed with saturated aqueous $NaHCO_3$ solution followed by brine solution and concentrated under vacuum to obtain a crude mixture which was purified by column chromatography (silica gel; ethyl acetate:petroleum ether) to obtain the desired nitrosporeusine compound of formula I.

Example 1

Synthesis of 4-hydroxy-5, 6-dihydroclopenta[c] pyrrole-1, 3 (2H, 4H)-dione (4)

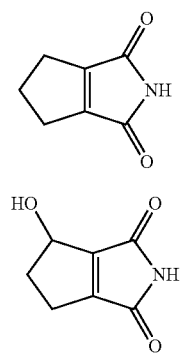

To a solution of compound 3 (0.10 g, 0.73 mmol) in dry 1, 4-Dioxane (1.5 mL) was added $SeO_2$ (0.32 g, 2.91 mmol) and was subjected to microwave irradiation at 110° C. for 30 min. (Antonpaarmonowave 300 instrument). The reaction mixture was evaporated to dryness and the crude obtained was purified by silica gel column chromatography with elution of 50-70% EtOAc:Pet Ether to obtain product 4 (30 mg) in 61% yield (based on recovered starting material). Unreacted starting material was recovered (54 mg).

$^1$H NMR: (δ ppm, 400 MHz) $D_2O$: 2.60-2.64 (m, 1H), 2.99-3.12 (m, 1H), 3.18 (m, 2H), 5.53-5.56 (m, 1H); $^{13}$C NMR: (δ ppm, 100 MHz) $D_2O$: 24.0, 37.3, 69.8, 152.0, 152.9, 169.0, 169.7

The racemic alcohol (4) obtained above has been subjected to enzymatic resolution with amano lipase PS and vinyl acetate which gave (+) 4-hydroxy-5,6-dihydroclopenta [c]pyrrole-1,3 (2H, 4H)-dione as single enantiomer with 98% enantiomeric excess as shown in example 2.

Example 2

Synthesis of (S)-4-Hydroxy-5,6-dihydrocyclopenta [c]pyrrole-1,3(2H,4H)-dione ((+)-4)

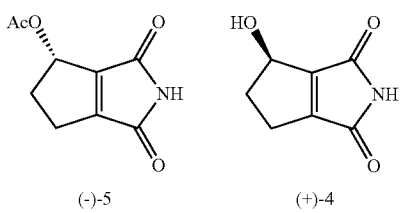 [SMILES: CC(=O)O[C@H]1CCC2=C1C(=O)NC2=O ; O=C1NC(=O)C2=C1CC[C@H]2O]

To a solution of alcohol 4 (1.12 g, 7.32 mmol) in dry THF was added Amano PS lipase (1.0 g) followed by addition of vinyl acetate (3.3 mL, 36.6 mmol) and stirred at room temperature for 10 h. The reaction was monitored by chiral HPLC analysis (Chiralpak IB column,) and upon 50% conversion, the reaction mixture was filtered through celite bed, concentrated and was added with 10 mL of water. The aqueous layer was extracted thrice with EtOAc (3×10 mL) and combined organic layer was washed with brine, dried over anhydrous $Na_2SO_4$ and concentrated in vacuo to obtain crude mixture of alcohol and acetate which on chromatographic separation yielded (R)-1,3-dioxo-1,2,3,4,5,6-hexahydrocyclopenta[c]pyrrol-4-yl (−)-5 (0.538 g) in 38% yield as white solid and (+)-(S)-4-hydroxy-5,6-dihydrocyclopenta [c]pyrrole-1,3(2H,4H)-dione (+)-4 (0.518 g) with 98% ee in 47% yield as white solid. HPLC conditions: Chiralpak IB column, Petroleum ether/2-propanol=95:5, flow rate=1 mL/min, 230 nm UV detector, $t_1$=46.2 min (minor) and $t_2$=51.9 min (major).

(−)-5 $[α]_D^{26}$ −38.3 (c 0.77 in $CHCl_3$), $^1$H NMR (200 MHz, $CDCl_3$); δ7.43 (br s, 1H), 5.96-5.91 (m, 1H), 2.92-2.64 (m, 3H), 2.32-2.27 (m, 1H), 2.02 (s, 3H); $^{13}$C NMR (100 MHz, $CDCl_3$): δ 170.1, 165.7, 165.6, 164.8, 159.2, 149.8, 72.0, 36.1, 25.1, 20.9.

(+)-4 $[α]_D^{26}$ +56.1 (c 1.07 in MeOH), $^1$H NMR (200 MHz, $D_2O$); δ5.21-5.10 (m, 1H), 2.91-2.67 (m, 2H), 2.65-2.47 (m, 1H), 2.31-2.13 (m, 1H).

Example 3

Synthesis of (R)-4-Hydroxy-5,6-dihydrocyclopenta [c]pyrrole-1,3(2H,4H)-dione ((−)-4)

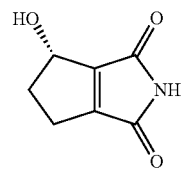

(-)-4

To a solution of acetate (−)-5 (0.10 g, 0.50 mmol) in acetone was added Amano PS lipase (0.08 g) and phosphate buffer (10 mL) of pH 7 and warmed at 40° C. for 3 h. The reaction mixture was then concentrated in vacuo to remove acetone and extracted twice with EtOAc (2×4 mL). The combined organic layer was washed with brine, dried over anhydrous $Na_2SO_4$ and concentrated to obtain crude residue which was subjected to chromatographic separation to yield (−)-4 (0.072 g) as white solid with 99% ee in 92% yield. $[α]_D^{25}$ −53.41 (c 1.34 in MeOH), $^1$H NMR (200 MHz, $D_2O$): δ5.22-5.08 (m, 1H), 2.92-2.66 (m, 2H), 2.65-2.48 (m, 1H), 2.31-2.13 (m, 1H); HPLC condition: Chiralpak IB column, Petroleum ether/2-propanol=95:5, 1 mL/min, 230 nm UV detector, $t_1$=46.2 min (major) and $t_2$=51.9 min (minor).

Example 4

Synthesis of (R)-1,3-Dioxo-1,2,3,4,5,6-hexahydro-cyclopenta[c]pyrrol-4-yl acetate ((+)-5)

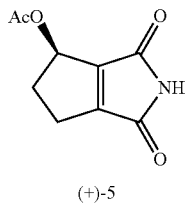

(+)-5

To a solution of alcohol (+)-4 (0.10 g, 0.65 mmol) in dry CH$_2$Cl$_2$ (3.0 mL) was added pyridine (0.102 mL, 1.300 mmol) and Ac$_2$O (0.066 mL, 0.65 mmol). The reaction mixture was stirred at room temperature for 10 h. Then the reaction mixture was diluted with water (3.0 mL) and extracted with CH$_2$Cl$_2$ (3×3 mL). The combined organic layer was washed with 1N HCl and then with brine solution, dried over anhydrous Na$_2$SO$_4$ and concentrated in vacuo to obtain crude residue which was subjected to chromatographic separation (30% EtOAc:Petroleum ether) to yield (+)-5 (0.105 g) as white solid with 82% yield. $[\alpha]_D^{26}$ +40.1 (c 0.54 in CHCl$_3$), $^1$H NMR (200 MHz, CDCl$_3$): δ7.43 (br s, 1H), 5.96-5.91 (m, 1H), 2.92-2.64 (m, 3H), 2.32-2.27 (m, 1H), 2.02 (s, 3H); $^{13}$C NMR (100 MHz, CDCl$_3$): δ170.1, 165.7, 165.6, 164.8, 159.2, 149.8, 72.0, 36.1, 25.1, 20.9.

Example 5

Synthesis of 4-hydroxybenzothioic S-acid (6)

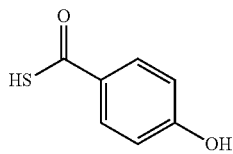

To a solution of 4-hydroxy benzoic acid (0.50 g, 3.62 mmol) in dry acetonitrile (5 mL) was added Lawesson's reagent (0.73 g, 1.81 mmol) and was subjected to microwave irradiation at 100° C. for 15 min. (Antonpaarmonowave 300 instrument). The reaction mixture was evaporated to dryness to obtain crude compound which was washed several times with 1N HCl, then with brine solution and dried over anhydrous sodium sulphate. The combined organic layer was concentrated in vacuo and purified by silica gel column chromatography with elution of 20-30% EtOAc: Petroleum Ether to obtain the 4-hydroxybenzothioic S-acid (6) (300 mg) in 53% yield. $^1$H NMR: (δ ppm, 200 MHz) CDCl$_3$:3.58 (br. s, 1H), 6.88 (d, J=8 Hz, 2H), 7.85 (d, J=8 Hz, 2H)

Example 6

Synthesis of S-((3aS*,6S*,6aR*)-6-hydroxy-1,3-dioxohexahydrocyclopenta[c]pyrrol-3a(1H)-yl) 4-hydroxybenzothioate (Nitrosporeusine A (1)) and S-((3aS*,6R*,6aR*)-6-hydroxy-1,3-dioxohexahydrocyclopenta[c]pyrrol-3a(1H)-yl) 4-hydroxybenzothioate (Nitrosporeusine B (2))

A round-bottomed flask equipped with a magnetic stirrer, was charged with 4-hydroxybenzothioic S-acid (6)(0.10 g, 0.57 mmol), compound (4) (0.08 g, 0.52 mmol), and water (2.0 mL). The reaction mixture was stirred vigorously at room temperature i.e. 25° C. for 12 h. The progress of reaction was monitored by TLC analysis, which was then diluted with ethyl acetate and extracted thrice (3×2 mL). The combined organic layer was washed with saturated aqueous NaHCO$_3$ followed by brine solution and dried over anhydrous Na$_2$SO$_4$. The crude compound obtained was subjected to column chromatography (60-70% EtOAc: petroleum ether) to give a 3:1 diastereomeric mixture of compound 2 (100 mg) and compound 1 (30 mg), respectively, as white solids in 65% overall yield.

Compound (1): $^1$H NMR: (δ ppm, 400 MHz) DMSO-D$_6$: 11.28 (br. s., 1H), 7.74 (d, J=8.02 Hz, 2H), 6.85 (d, J=8.02 Hz, 2H), 5.30-5.31 (m, 1H), 4.47 (br. s., 1H), 3.25 (d, J=7.3 Hz, 1H), 2.20-2.28 (m, 2H), 1.90-1.92 (m, 2H), 1.69-1.71 (m, 2H); $^{13}$C NMR: (δ ppm, 100 MHz) DMSO-D$_6$: 190.0, 179.1, 175.2, 163.6, 130.0, 127.0, 116.2, 72.3, 60.2, 59.2, 35.06, 32.8

Compound (2) $^1$H NMR: (δ ppm, 400 MHz) DMSO-D$_6$: 11.54 (s, 1H), 10.65 (s, 1H), 7.74 (d, J=8.02 Hz, 2H), 6.88 (d, J=8.02 Hz, 2H), 5.30-5.26 (m, 1H), 4.38-4.39 (m, 1H), 3.11 (br. s, 1H), 2.22-2.17 (m, 2H), 1.83-1.78 (m, 1H), 1.62-1.56 (m, 1H); $^{13}$C NMR: (δ ppm, 100 MHz) DMSO D$_6$: 190.4, 179.3, 176.9, 163.7, 130.0, 126.8, 116.2, 74.5, 63.9, 58.1, 33.8, 32.4.

Example 7

Synthesis of S-((3aS,6S,6aR)-6-hydroxy-1,3-dioxohexahydrocyclopenta[c]pyrrol-3a(1H)-yl) 4-hydroxybenzothioate ((+)1) and S-((3aR,6S,6aS)-6-hydroxy-1,3-dioxohexahydrocyclopenta[c]pyrrol-3a(1H)-yl) 4-hydroxybenzothioate ((−)2)

Nitrosporeusine A (+)1$[\alpha]_D^{27}$ +49.3 (c 0.51, MeOH); $^1$H NMR (500 MHz, CD$_3$OD): 7.81 (d, J=8.9 Hz, 2H), 6.87 (d, J=8.9 Hz, 2H), 4.65-4.63 (m, 1H), 3.40 (d, J=7.6 Hz, 1H), 2.42-2.40 (m, 1H), 2.12-2.05 (m, 2H), 1.87-1.85 (m, 1H); $^{13}$C NMR (125 MHz, CD$_3$OD): δ191.0, 181.5, 177.3, 164.9, 130.9, 128.8, 116.7, 73.9, 61.3, 60.4, 35.2, 33.7.

Nitrosporeusine B(−)2 $[\alpha]_D^{27}$ −121.8 (c 0.61, MeOH); $^1$H NMR (500 MHz, CD$_3$OD): δ7.81 (d, J=8.9 Hz, 2H), 6.86 (d, J=8.9 Hz, 2H), 4.57-4.55 (m, 1H), 3.27 (brs, 1H), 2.38-2.30 (m, 2H), 1.95-1.94 (m, 1H), 1.77-1.74 (m, 1H); $^{13}$C NMR (125 MHz, CD$_3$OD): δ192.4, 181.6, 178.5, 164.9, 130.9, 128.8, 116.7, 76.4, 65.5, 59.6, 34.7, 33.4.

Example 8

Synthesis of S-((3aR,6R,6aS)-6-hydroxy-1,3-dioxohexahydrocyclopenta[c]pyrrol-3a(1H)-yl) 4-hydroxybenzothioate ((−)1) and S-((3aS,6R,6aR)-6-hydroxy-1,3-dioxohexahydrocyclopenta[c]pyrrol-3a(1H)-yl) 4-hydroxybenzothioate ((+)2)

Nitrosporeusine A (−)1: $[\alpha]_D^{27}$ −56.5 (c 0.25 in MeOH); $^1$H NMR (500 MHz, CD$_3$OD): δ7.81 (d, J=8.9 Hz, 2H), 6.87

(d, J=8.9 Hz, 2H), 4.65-4.63 (m, 1H), 3.40 (d, J=7.6 Hz, 1H), 2.42-2.40 (m, 1H), 2.12-2.05 (m, 2H), 1.87-1.85 (m, 1H); $^{13}$C NMR (125 MHz, CD$_3$OD): δ191.0, 181.5, 177.3, 164.9, 130.9, 128.8, 116.7, 73.9, 61.3, 60.4, 35.2, 33.7.

Nitrosporeusine B(+)2: $[α]_D^{27}$ +125.2 (c 0.31 in MeOH); $^1$H NMR (500 MHz, CD$_3$OD): δ7.81 (d, J=8.9 Hz, 2H), 6.86 (d, J=8.9 Hz, 2H), 4.57-4.55 (m, 1H), 3.27 (br s, 1H), 2.38-2.30 (m, 2H), 1.95-1.94 (m, 1H), 1.77-1.74 (m, 1H); $^{13}$C NMR (125 MHz, CD$_3$OD): δ192.4, 181.6, 178.5, 164.9, 130.9, 128.8, 116.7, 76.4, 65.5, 59.6, 34.7, 33.4.

Example 9

Synthesis of S-((3aR*,6R*,6aS*)-6-Hydroxy-1,3-dioxohexahydrocyclopenta[c] pyrrol-3a(1H)-yl) ethanethioate (7)

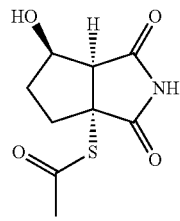

7

20 mg obtained as white solid. IR (neat) v$_{max}$ 3809, 1708, 1692, 1515 cm$^{-1}$; $^1$H NMR (400 MHz, CD$_3$OD): δ 4.60-4.56 (m, 1H), 3.34-3.30 (d, 1H), 2.33 (s, 3H), 2.31-2.28 (m, 1H) 2.02-1.89 (m, 1H), 1.88-1.81 (m, 1H), 1.79-1.77 (m, 1H); $^{13}$C NMR (100 MHz, CD$_3$OD): δ 198.0, 181.0, 177.1, 73.9, 61.0, 60.7, 35.2, 33.4, 29.8; HRMS (ESI): m/z calculated for C$_9$H$_{11}$NO$_4$S[M+Na]$^+$ 252.0301, found 252.0299.

Example 10

Synthesis of S-((3aS*,6R*,6aR*)-6-Hydroxy-1,3-dioxohexahydrocyclopenta[c] pyrrol-3a(1H)-yl) ethanethioate (8)

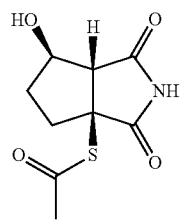

8

57 mg obtained as white solid. mp 120-129° C.; IR (neat) v$_{max}$ 3809, 1708, 1692, 1515 cm$^{-1}$; $^1$H NMR (400 MHz, CD$_3$OD): δ4.53-4.51 (m, 1H), 3.17-3.15 (d, 1H), 2.31 (s, 3H), 2.23-2.19 (m, 2H), 1.89-1.88 (m, 1H), 1.70-1.65 (m, 1H); $^{13}$C NMR (100 MHz, CD$_3$OD): δ196.9, 179.6, 176.7, 74.8, 63.6, 58.3, 32.9, 31.7, 28.0; HRMS (ESI): m/z calculated for C$_9$H$_{11}$NO$_4$S[M+Na]$^+$ 252.0301, found 252.0299.

Example 11

Synthesis of S-((3aR*,6R*,6aS*)-6-Hydroxy-1,3-dioxohexahydrocyclopenta[c] pyrrol-3a(1H)-yl) 2-phenylethanethioate (9)

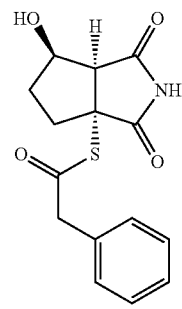

9

25 mg obtained as yellow solid. $^1$H NMR (400 MHz, CD$_3$OD): δ7.36-7.28 (m, 5H), 4.55-4.53 (m, 1H), 3.84 (s, 2H), 3.25-3.23 (d, J=7.6 Hz, 1H), 2.31-2.27 (m, 1H), 1.99-1.87 (m, 1H), 1.85-1.75 (m, 2H); $^{13}$C NMR (125 MHz, CD$_3$OD): δ199.9, 181.0, 177.1, 134.5, 131.0, 129.9, 128.8, 73.9, 61.0, 50.3, 49.7, 35.2, 33.5; HRMS (ESI): m/z calculated for C$_{15}$H$_{15}$NO$_4$S[M+Na]$^+$ 328.0614, found 328.0601.

Example 12

Synthesis of S-((3aS*,6R*,6aR*)-6-Hydroxy-1,3-dioxohexahydrocyclopenta[c] pyrrol-3a(1H)-yl) 2-phenylethanethioate (10)

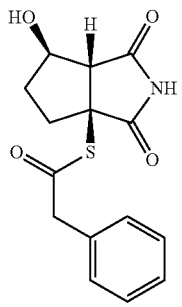

10

35 mg obtained as white solid. $^1$H NMR (500 MHz, CD$_3$OD): δ7.35-7.30 (m, 5H), 4.52-4.51 (m, 1H), 3.86 (s, 2H), 3.13 (s, 1H), 2.21-2.18 (m, 2H), 1.91-1.87 (m, 1H), 1.69-1.66 (m, 1H); $^{13}$C NMR (125 MHz, CD$_3$OD): δ198.9, 179.6, 176.7, 133.0, 129.5, 128.3, 127.2, 74.8, 63.6, 58.4, 48.6, 33.0, 31.7; ☐HRMS (ESI): m/z calculated for C$_{15}$H$_{15}$NO$_4$S[M+Na]$^+$ 328.0614, found 328.0601.

Example 13

Synthesis of S-((3aS*,6R*,6aR*)-6-Hydroxy-1,3-dioxohexahydrocyclopenta[c] pyrrol-3a(1H)-yl) 4-fluorobenzothioate (11)

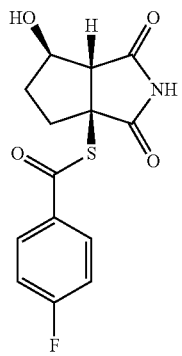

11

50 mg obtained as brown solid, mp 184-186° C.; IR (neat) $v_{max}$ 3314, 2934, 1798, 1024 cm$^{-1}$; $^1$H NMR (400 MHz, CD$_3$OD): δ8.02-7.98 (m, 2H), 7.29-7.24 (m, 2H), 4.59-4.58 (m, 1H), 3.34-3.28 (m, 1H), 2.40-2.33 (m, 2H), 1.98-1.95 (m, 1H), 1.84-1.69 (m, 1H); $^{13}$C NMR (100 MHz, CD$_3$OD): δ91.1, 179.5, 176.7, 167.6, 132.2, 132.2, 129.8, 129.7, 115.8, 115.6, 74.8, 63.7, 58.3, 33.2, 31.8; HRMS (ESI): m/z calculated for C$_{14}$H$_{12}$NO$_4$SF[M+Na]$^+$ 332.0363 found 332.0361.

Example 14

Synthesis of S-((3aS*,6R*,6aR*)-6-Hydroxy-1,3-dioxohexahydrocyclopenta[c] pyrrol-3a(1H)-yl) thiophene-2-carbothioate (12)

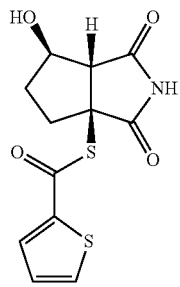

12

70 mg obtained as white solid. IR (neat) $v_{max}$ 3808, 1741, 1706, 1693, 1515 cm$^{-1}$; $^1$H NMR (400 MHz, CD$_3$OD): δ7.91-7.87 (m, 2H), 7.23-7.20 (dd, J=4.8, 4.0 Hz, 1H), 4.58-4.57 (m, 1H), 3.31-3.30 (d, 1H), 2.36-2.30 (m, 2H), 1.95-1.94 (m, 1H), 1.76-1.73 (m, 1H); $^{13}$C NMR (100 MHz, CD$_3$OD): δ182.8, 177.9, 175.1, 138.5, 132.7, 130.7, 126.7, 73.4, 62.3, 56.9, 31.7, 30.3; HRMS (ESI): m/z calculated for C$_{12}$H$_{11}$NO$_4$S$_2$ [M+Na]$^+$ 320.0002, found 320.0008.

Example 15

Synthesis of S-((3aS*,6S*,6aR*)-6-Hydroxy-1,3-dioxohexahydrocyclopenta[c] pyrrol-3a(1H)-yl) 2-chlorobenzothioate (13)

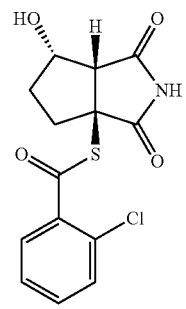

13

26 mg obtained as white solid, mp 173-174° C.; IR (neat) $v_{max}$ 3743, 2925, 2320, 1707, 1515 cm$^{-1}$; $^1$H NMR (400 MHz, CD$_3$OD): δ7.72-7.69 (m, 1H), 7.55-7.53 (m, 2H), 7.45-7.43 (m, 1H), 4.67-4.63 (m, 1H), 3.47-3.45 (d, J=7.6 Hz, 1H), 2.43-2.39 (m, 1H), 2.08-1.99 (m, 2H), 1.86-1.83 (m, 1H); $^{13}$C NMR (100 MHz, CD$_3$OD): δ196.0, 183.0, 179.3, 139.7, 136.9, 134.6, 134.3, 133.0, 130.9, 76.3, 64.0, 63.3, 37.7, 35.9; HRMS (ESI): m/z calculated for C$_{14}$H$_{12}$NO$_4$ClS[M+Na]$^+$ 348.0068, found 348.0061.

Example 16

Synthesis of S-((3aS*,6R*,6aR*)-6-Hydroxy-1,3-dioxohexahydrocyclopenta[c] pyrrol-3a(1H)-yl) 2-chlorobenzothioate (14)

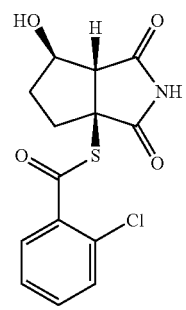

14

82 mg obtained as white solid. mp 154-158° C.; IR (neat) $v_{max}$ 3743, 2925, 2320, 1707, 1515 cm$^{-1}$; $^1$H NMR (200 MHz, CD$_3$OD): δ7.78-7.76 (m, 1H), 7.58-7.50 (m, 3H), 4.63-4.60 (td, J=3.7, 1.2 Hz, 1H), 2.39-2.31 (m, 2H), 1.97-1.95 (m, 1H), 1.82-1.80 (m, 1H); $^{13}$C NMR (100 MHz, CDCl$_3$): δ192.6, 178.3, 176.1, 135.0, 133.2, 131.3, 131.1, 129.9, 126.9, 75.4, 63.7, 59.2, 33.2, 32.5; HRMS (ESI): m/z calculated for C$_{14}$H$_{12}$NO$_4$ClS[M+Na]$^+$ 348.0068, found 348.0061.

Example 17

Synthesis of S-((3aR*,6R*,6aS*)-6-Hydroxy-1,3-dioxohexahydrocyclopenta[c] pyrrol-3a(1H)-yl) benzothioate (15)

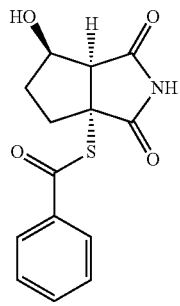

15

26 mg as white solid. mp 185-186° C.; IR (neat) $v_{max}$ 3743, 2927, 2320, 1741, 1706, 1531 cm$^{-1}$; $^1$H NMR (400 MHz, CD$_3$OD): δ7.91-7.89 (dd, J=8.4, 1.1 Hz, 2H), 7.66-7.64 (m, 1H), 7.53-7.49 (m, 2H), 4.62-4.59 (m, 1H), 3.42 (d, J=7.6 Hz, 1H), 2.42-2.39 (dd, J=13.2, 7.1 Hz, 1H), 2.08-2.02 (m, 2H), 1.84-1.82 (m, 1H); $^{13}$C NMR (100 MHz, CD$_3$OD): δ193.6, 181.1, 177.2, 137.4, 135.6, 130.3, 128.4, 73.9, 61.1, 60.6, 35.3, 33.7; HRMS (ESI): m/z calculated for C$_{14}$H$_{13}$NO$_4$S[M+Na]$^+$ 314.0457, found 314.0456.

Example 18

Synthesis of S-((3aS*,6R*,6aR*)-6-Hydroxy-1,3-dioxohexahydrocyclopenta[c] pyrrol-3a(1H)-yl) benzothioate (16)

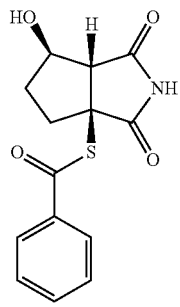

16

36 mg as white solid. mp 180-182° C.; IR (neat) $v_{max}$ 3743, 2927, 2320, 1741, 1706, 1531 cm$^{-1}$; $^1$H NMR (400 MHz, CD$_3$OD): δ7.94-7.91 (m, 2H), 7.69-7.66 (m, 1H), 7.54-7.51 (m, 2H), 4.59-4.58 (m, 1H), 3.34-3.42 (m, 1H), 2.40-2.33 (m, 2H), 1.96-1.95 (m, 1H), 1.78-1.77 (m, 1H); $^{13}$C NMR (100 MHz, CD$_3$OD): δ191.1, 178.1, 175.27, 134.21, 132.54, 127.23, 125.36, 73.36, 62.28, 56.75, 31.75, 30.32; HRMS (ESI): m/z calculated for C$_{14}$H$_{13}$NO$_4$S[M+Na]$^+$ 314.0457, found 314.0456.

Example 19

Synthesis of S-((3aS*,6R*,6aR*)-6-Hydroxy-1,3-dioxohexahydrocyclopenta[c] pyrrol-3a(1H)-yl) 2-hydroxybenzothioate (17)

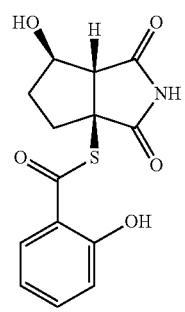

17

23 mg obtained as white solid, mp 213-216° C.; IR (neat) $v_{max}$ 2935, 2827, 1823, 1448, 1023 cm$^{-1}$; $^1$H NMR (400 MHz, CD$_3$OD): δ7.85-7.84 (m, 1H), 7.55-7.51 (m, 1H), 6.98-6.95 (m, 2H), 4.59 (m, 1H), 3.34-3.32 (d, 1H), 2.41-2.33 (m, 2H), 2.00-1.96 (m, 1H), 1.78-1.75 (m, 1H);

$^{13}$C NMR (100 MHz, CD$_3$OD): δ196.0, 179.6, 176.6, 158.9, 136.1, 128.8, 119.7, 119.3, 117.6, 75.0, 63.7, 58.26, 33.1, 31.7; HRMS (ESI): m/z calculated for C$_{14}$H$_{13}$NO$_5$S [M+Na]$^+$ 330.0407, found 330.0405.

Example 20

Synthesis of S-((3aR*,6aS*)-1,3-Dioxohexahydrocyclopenta[c]pyrrol-3a(1H)-yl) ethanethioate (18)

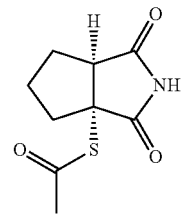

18

71 mg obtained as white solid, mp 120-122° C.; $^1$H NMR (400 MHz, CDCl$_3$): δ8.96 (br s, 1H), 3.27-3.24 (d, J=8.8 Hz, 1H), 2.34 (s, 3H), 2.32-2.24 (m, 2H), 1.83-1.54 (m, 4H); $^{13}$C NMR (100 MHz, CDCl$_3$): δ196.3, 178.2, 178.2, 59.5, 54.7, 36.2, 29.7, 29.6, 24.3; HRMS (ESI): m/z calculated for C$_9$H$_{11}$NO$_3$S[M+Na]$^+$ 236.0348, found 236.0352.

Example 21

Synthesis of S-((3aR*,6aS*)-1,3-Dioxohexahydro-cyclopenta[c]pyrrol-3a(1H)-yl) 2-phenylethanethioate (19)

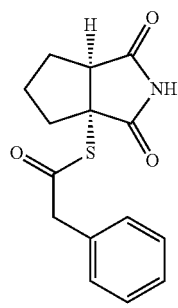

80 mg obtained as sticky liquid. $^1$H NMR (400 MHz, CDCl$_3$): δ8.50 (br s, 1H), 7.96-7.89 (m, 2H), 7.18-7.09 (m, 2H), 3.39-3.35 (dd, J=8.8, 0.6 Hz, 1H), 2.42-2.27 (m, 2H), 2.09-1.95 (m, 4H), 1.91-1.56 (m, 2H); $^{13}$C NMR (100 MHz, CDCl$_3$): δ198.3, 178.1, 178.1, 132.4, 129.7, 128.9, 127.8, 59.6, 54.8, 49.5, 36.3, 29.8, 24.3; HRMS (ESI): m/z calculated for C$_{15}$H$_{15}$NO$_3$S[M+Na]$^+$ 312.0665, found 312.0657.

Example 22

Synthesis of S-((3aR*,6aS*)-1,3-Dioxohexahydro-cyclopenta[c]pyrrol-3a(1H)-yl) 4-fluorobenzothioate (20)

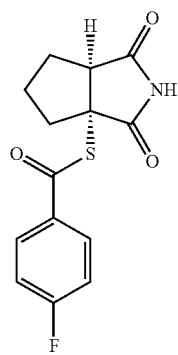

40 mg as white solid, mp 186-187° C.; IR (neat) v$_{max}$ 3744, 2922, 1770, 1647 cm$^{-1}$; $^1$H NMR (400 MHz, CDCl$_3$): δ8.40 (br s, 1H) 7.96-7.89 (m, 2H), 7.18-7.08 (m, 2H), 3.39-3.35 (m, 1H), 2.48-2.28 (m, 2H), 2.09-1.91 (m, 2H), 1.64-1.59 (m, 2H); $^{13}$C NMR (100 MHz, CDCl$_3$): δ190.6, 178.3, 178.2, 167.6, 165.1, 131.9, 130.1, 130.0, 116.1, 116.0, 59.5, 55.0, 36.5, 29.8, 29.8, 24.5; HRMS (ESI): m/z calculated for C$_{14}$H$_{12}$NO$_3$FS[M+Na]$^+$ 316.0414, found 316.0408.

Example 23

Synthesis of S-((3aR*,6aS*)-1,3-Dioxohexahydro-cyclopenta[c]pyrrol-3a(1H)-yl) 2-chlorobenzothioate (21)

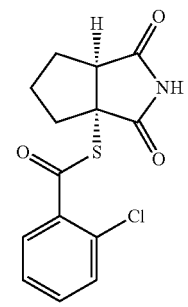

31 mg obtained as white solid, mp 188-190° C.; IR (neat) v$_{max}$ 3229, 1707, 1675, 1547 cm$^{-1}$; $^1$H NMR (400 MHz, CDCl$_3$): δ8.88 (br s, 1H), 7.72-7.70 (d, J=7.8 Hz, 1H), 7.44-7.43 (m, 2H), 7.35-7.33 (m, 1H), 3.44-3.42 (d, J=8.8 Hz, 1H), 2.41-2.38 (m, 1H), 2.31-2.30 (m, 1H), 1.95-1.93 (m, 1H), 1.92-1.90 (m, 2H), 1.63-1.61 (m, 1H); $^{13}$C NMR (100 MHz, CDCl$_3$): δ191.9, 178.1, 177.9, 135.3, 133.1, 131.4, 131.1, 129.7, 126.7, 60.3, 54.8, 36.4, 29.8, 24.5; HRMS (ESI): m/z calculated for C$_{14}$H$_{12}$NO$_3$ClS[M+Na]$^+$ 332.0109, found 332.0119.

Example 24

Synthesis of S-(1,3-Dioxo-2,3,4,5-tetrahydrocyclopenta[c]pyrrol-3a(1H)-yl) 4-fluorobenzothioate (22)

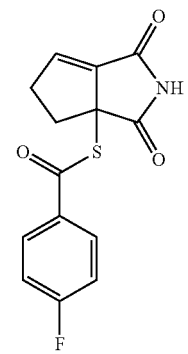

35 mg obtained as white solid, mp 191-192° C.; IR (neat) v$_{max}$ 3159, 2979, 1714, 1661, 1594, 1200 cm$^{-1}$; $^1$H NMR (200 MHz, CDCl$_3$): δ7.97-7.89 (m, 3H), 7.17-7.09 (m, 2H), 6.92-6.89 (dd, J=4.0, 2.0 Hz, 1H), 3.23-3.14 (m, 1H), 2.87-2.85 (m, 1H), 2.59-2.56 (m, 2H); $^{13}$C NMR (100 MHz, CDCl$_3$): δ188.9. 173.1, 163.3, 140.5, 132.4, 130.2, 130.1, 116.1, 115.9, 63.6, 37.2, 36.0; HRMS (ESI): m/z calculated for C$_{14}$H$_{10}$NO$_3$FS[M+Na]$^+$314.0258, found 314.0250.

Example 25

Synthesis of S,S'-((3aR*,6aR*)-1,3-Dioxohexahydrocyclopenta[c]pyrrole-3a,6(1H)-diyl) bis(4-fluorobenzothioate) (23)

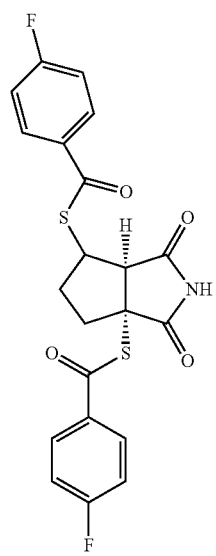

23

35 mg obtained as sticky liquid. $^1$H NMR (200 MHz, CDCl$_3$): δ8.35 (br s, 1H), 7.98-7.92 (m, 4H), 7.19-7.09 (m, 4H), 4.62-4.60 (m, 1H), 3.53-3.52 (t, J=1.4 Hz, 1H), 2.50-2.29 (m, 1H), 2.29-2.01 (m, 4H); $^{13}$C NMR (100 MHz, CDCl$_3$): δ190.5, 188.4, 177.2, 174.8, 167.8, 167.4, 165.2, 164.9, 132.7, 131.7, 131.6, 130.3, 130.2, 130.0, 129.9, 116.2, 116.1, 115.8, 60.7, 58.7, 46.7, 34.6, 31.5, 29.7; HRMS (ESI): m/z calculated for C$_{21}$H$_{15}$NO$_4$F$_2$S$_2$[M+Na]$^+$ 470.0285, found 470.0293.

Example 26

Synthesis of S-(1,3-Dioxo-1,2,3,4,5,6-hexahydrocyclopenta[c]pyrrol-4-yl) benzothioate (24)

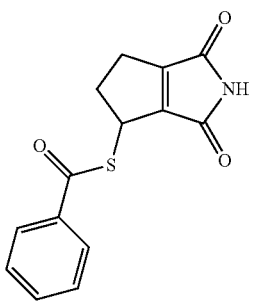

24

30 mg obtained as white solid, mp 149-151° C.; IR (neat) v$_{max}$ 3806, 2922, 1707, 1676, 1532 cm$^{-1}$; $^1$H NMR (200 MHz, CDCl$_3$): δ7.94 (dd, J=8.4, 1.3 Hz, 2H), 7.64-7.43 (m, 3H), 7.23 (br s, 1H), 5.09-5.02 (m, 1H), 3.28-3.21 (m, 1H), 2.8-2.80 (m, 2H), 2.61-2.50 (m, 1H); $^{13}$C NMR (100 MHz, CDCl$_3$): δ190.2, 165.5, 164.7, 156.5, 151.4, 136.2, 133.9, 128.8, 127.4, 41.5, 38.3, 25.7; HRMS (ESI): m/z calculated for C$_{14}$H$_{11}$NO$_3$S[M+Na]$^+$ 296.0352, found 296.0345.

Example 27

Synthesis of S,S'-((3aS*,6aS*)-1,3-Dioxohexahydrocyclopenta[c]pyrrole-3a,6(1H)-diyl) dibenzothioate (25)

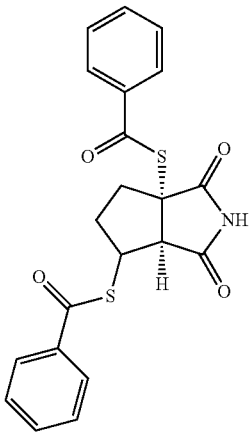

25

35 mg obtained as sticky liquid. $^1$H NMR (200 MHz, CDCl$_3$): δ8.45 (br s, 1H), 7.98-7.87 (m, 4H), 7.50-7.47 (m, 2H), 7.46-7.41 (dd, J=7.5, 1.7 Hz, 4H), 4.63-4.61 (m, 1H), 3.53 (s, 1H), 2.51-2.14 (m, 4H); $^{13}$C NMR (100 MHz, CDCl$_3$): δ192.1, 190.0, 177.4, 174.9, 136.4, 135.3, 134.4, 133.8, 128.9, 128.7, 127.6, 127.5, 60.7, 58.6, 46.6, 34.6, 31.6.

Example 28

Synthesis of S-(1,3-Dioxo-2,3,4,5-tetrahydrocyclopenta[c]pyrrol-3a(1H)-yl)ethanethioate (26)

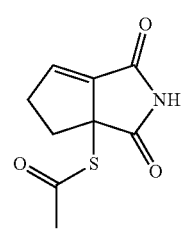

26

40 mg obtained as white solid, mp 170-172° C.; IR (neat) v$_{max}$ 3744, 2924, 2854, 1707, 1515, 1462 cm$^{-1}$; $^1$H NMR (400 MHz, CDCl$_3$): δ8.18 (br s, 1H), 6.85 (dd, J=4.2, 2.0 Hz, 1H), 3.16-3.13 (m, 1H), 2.80-2.75 (m, 1H), 2.48-2.37 (m, 2H), 2.32 (s, 3H); $^{13}$C NMR (100 MHz, CDCl$_3$): δ194.5, 173.1, 163.1, 140.4, 140.3, 63.8, 36.8, 35.9, 30.4; HRMS (ESI): m/z calculated for C$_9$H$_9$NO$_3$S[M+Na]$^+$ 234.0195, found 234.0194.

Example 29

Synthesis of S-(1,3-Dioxo-2,3,4,5-tetrahydrocyclopenta[c]pyrrol-3a(1H)-yl) 2-phenylethanethioate (27)

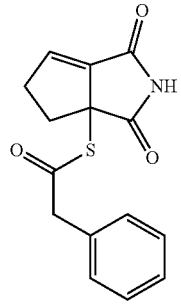

30 mg obtained as white solid, mp 155-158° C.; IR (neat) $v_{max}$ 3200, 2923, 1764, 1693, 1267 cm$^{-1}$; $^1$H NMR (200 MHz, CDCl$_3$): δ7.86 (br s, 1H),7.36-7.24 (m, H), 6.84-6.82 (m, 1H), 3.81 (s, 2H), 3.14-3.00 (m, 1H), 2.82-2.67 (m, 1H), 2.47-2.36 (m, 2H); $^{13}$C NMR (125 MHz, CDCl$_3$): δ196.1, 173.2, 163.4, 140.5, 140.4, 132.3, 129.8, 128.8, 127.8, 63.8, 50.2, 36.8, 35.9; HRMS (ESI): m/z calculated for C$_{15}$H$_{13}$NO$_3$S[M+Na]$^+$310.0508, found 310.0501.

Example 30

Synthesis of S,S'-((3aR*,6aR*)-1,3-Dioxohexahydrocyclopenta[c]pyrrole-3a,6(1H)-diyl) diethanethioate (28)

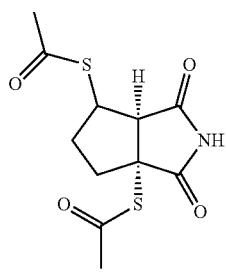

30 mg of compound as sticky solid. $^1$H NMR (200 MHz, CDCl$_3$): δ8.8 (br s, 1H), 4.37-4.35 (m, 1H), 3.27 (s, 1H), 2.34 (s, 3H), 2.32 (s, 1H), 2.10 (m, 4H); $^{13}$CNMR (100 MHz, CDCl$_3$):

δ196.3, 193.3, 177.22, 174.7, 60.2, 58.7, 46.3, 34.1, 31.6, 30.7, 29.6 HRMS (ESI): m/z calculated for C$_{11}$H$_{13}$NO$_4$S$_2$ [M+Na]$^+$ 310.0178, found 310.0171.

Example 31

Synthesis of S-(1,3-Dioxo-1,2,3,4,5,6-hexahydrocyclopenta[c]pyrrol-4-yl) thiophene-2-carbothioate (29)

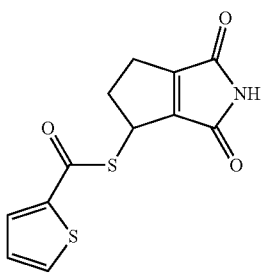

38 mg obtained as white solid, mp 138-139° C.; IR (neat) $v_{max}$ 2921, 2853, 1709, 1647, 1461 cm$^{-1}$; $^1$H NMR (200 MHz, CDCl$_3$): δ7.79 (d, J=3.9 Hz, 1H), 7.69-7.65 (m, 1H), 7.16-7.11 (m, 2H), 5.03-4.96 (m, 1H), 3.30-3.16 (m, 1H), 2.85-2.79 (m, 2H), 2.76-2.51 (m, 1H); $^{13}$C NMR (100 MHz, CDCl$_3$): δ182.1, 165.5, 164.8, 156.6, 151.1, 141.0, 133.5, 131.8, 128.1, 41.7, 38.3, 25.8; HRMS (ESI): m/z calculated for C$_{12}$H$_9$NO$_3$S$_2$ [M+Na]$^+$ 301.9916, found 301.9910.

Example 32

Synthesis of 1(3aS*,6aR*)-1,3-Dioxo-6a-((thiophene-2-carbonyl)thio) octahydrocyclopenta[c]pyrrol-4-yl acetate (30)

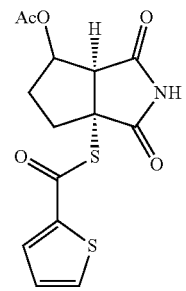

49 mg obtained as solid. mp 140-141° C.; IR (neat) $v_{max}$ 3830, 2922, 2853, 1737, 1707, 1646, 1514, 1210 cm$^{-1}$; $^1$H NMR (400 MHz, CDCl$_3$): δ8.78 (br s, 1H), 7.80-7.69 (d, J=3.9 Hz, 1H), 7.70-7.69 (d, J=4.9 Hz, 1H), 7.15-7.12 (m, 1H), 5.53-5.52 (d, J=3.9 Hz, 1H), 3.56-3.49 (m, 1H), 2.49-2.43 (m, 1H), 2.26-2.24 (m, 1H), 2.11-2.10 (m, 4H), 2.07-2.06 (m, 1H); $^{13}$C NMR (100 MHz, CDCl$_3$): δ183.8, 177.3, 173.6, 169.8, 140.0, 134.4, 134.3, 132.5, 128.3, 61.0, 58.5, 55.6, 33.6, 30.4, 30.1, 29.7, 21.1; HRMS (ESI): m/z calculated for C$_{14}$H$_{13}$NO$_5$S2[M+Na]$^+$ 340.0302, found 340.0308.

Example 33

Synthesis of (3aS*,6aR*)-6a-(Acetylthio)-1,3-dioxooctahydrocyclopenta[c]pyrrol-4-yl acetate (31)

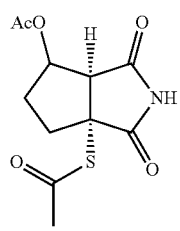

31

60 mg obtained as white solid. $^1$H NMR (200 MHz, CDCl$_3$): δ8.45 (br s, 1H), 5.53-5.35 (m, 1H), 3.67-3.43 (m, 1H), 2.39-2.37 (m, 4H), 2.35-2.09 (m, 4H), 1.93-1.82 (m, 2H); $^{13}$C NMR (100 MHz, CDCl$_3$): δ196.6, 196.0, 177.8, 177.7, 174.0, 172.8, 170.5, 169.9, 73.6, 60.7, 58.7, 58.3, 55.1, 33.3, 31.4, 30.3, 29.9, 29.7, 29.6, 29.5, 21.0, 20.8; HRMS (ESI): m/z calculated for C$_{11}$H$_{13}$NO$_5$S[M+Na]$^+$ 294.0407, found 294.0402.

Example 34

Synthesis of (3aS*,6aR*)-1,3-Dioxo-6a-((2-phenylacetyl)thio) octahydrocyclopenta[c]pyrrol-4-yl acetate (32)

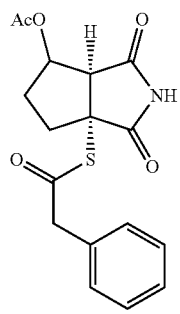

32

45 mg obtained as white solid. $^1$H NMR (400 MHz, CDCl$_3$): δ8.61-8.53 (br s, 1H), 7.31-7.17 (m, 5H), 5.39-5.23 (m, 1H), 3.72 (s, 2H), 3.51-3.27 (m, 1H), 2.28-2.25 (m, 1H), 2.15 (s, 3H), 2.01-1.94 (m, 1H), 1.70-1.68 (m, 2H); $^{13}$C NMR (100 MHz, CDCl$_3$): δ198.4, 197.9, 177.6, 173.7, 172.6, 170.5, 169.8, 132.2, 132.0, 129.8, 129.7, 128.8, 127.8, 73.6, 60.7, 58.7, 58.3, 55.1, 49.5, 49.3, 33.4, 31.5, 30.3, 29.8, 29.7, 21.0, 20.8 HRMS (ESI): m/z calculated for C$_{17}$H$_{17}$NO$_5$S[M+Na]$^+$ 370.0720, found 370.0717.

Example 35

Synthesis of (3aS*,6aR*)-6a-(4-Fluorobenzoyl) thio)-1,3-dioxooctahydrocyclopenta[c]pyrrol-4-yl acetate (33)

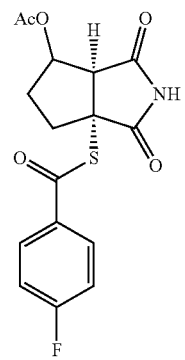

33

45 mg obtained as white solid. mp 118-119° C.; IR (neat) $v_{max}$ 3743, 3057, 2925, 1707, 1649, 1513 cm$^{-1}$; $^1$H NMR (400 MHz, CDCl$_3$): δ8.58-8.40 (br s, 1H), 8.00-7.93 (m, 2H), 7.23-7.14 (m, 2H), 5.58-5.43 (m, 1H), 3.79-3.55 (m, 1H), 2.51-2.32 (m, 2H), 2.20-2.11 (m, 4H), 1.96-1.87 (m, 1H); $^{13}$C NMR (100 MHz, CDCl$_3$): δ 190.0, 177.7, 177.6, 174.0, 169.9, 169.4, 165.4, 131.7, 130.2, 130.1, 116.2, 116.0, 73.6, 60.9, 58.6, 58.3, 55.3, 33.6, 31.8, 30.4, 29.9, 29.6, 21.0, 20.8 HRMS (ESI): m/z calculated for C$_{16}$H$_{14}$NO$_5$SF[M+Na]$^+$ 374.0456, found 374.0469.

Example 36

Synthesis of (3aS*,6aR*)-6a-(2-Chlorobenzoyl) thio)-1,3-dioxooctahydrocyclopenta[c]pyrrol-4-yl acetate (34)

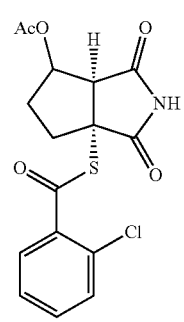

34

35 mg obtained as white solid, mp 90-91° C.; IR (neat) $v_{max}$ 3744, 1771, 1707, 1547, 1626 cm$^{-1}$; $^1$H NMR (400 MHz, CDCl$_3$): δ8.77 (br s, 1H), 7.74-7.73 (d, J=7.6 Hz, 1H), 7.47-7.37 (m, 2H), 7.36-7.33 (m, 1H), 5.55-5.54 (m, 1H), 3.57-3.56 (m, 1H), 2.46-2.43 (m, 1H), 2.26-2.25 (dt, J=13.3, 7.0 Hz, 1H), 2.16-2.13 (dd, J=6.6, 4.7 Hz, 1H), 2.11 (s, 3H), 2.09-1.91 (m, 1H); $^{13}$C NMR (100 MHz, CDCl$_3$): δ191.9, 177.2, 173.6, 169.9, 134.9, 133.3, 131.6, 129.9, 126.9, 73.6, 60.8, 59.0, 55.2, 33.4, 31.7, 30.4, 30.0, 21.0, 20.9; HRMS (ESI): m/z calculated for C$_{16}$H$_{14}$NO$_5$ClS[M+Na]$^+$ 390.0173, found 390.0158.

Example 37

Synthesis of (3aS*,6aR*)-6a-(Benzoylthio)-1,3-dioxooctahydrocyclopenta [c]pyrrol-4-yl acetate (35)

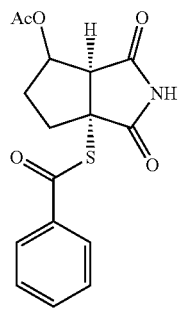

25 mg obtained as white solid. IR (neat) vmax 3743, 2922, 1737, 1707, 1675, 1546, 1208 cm$^{-1}$; $^1$H NMR (400 MHz, CDCl$_3$): δ9.05 (br s, 1H), 7.92-7.86 (m, 2H), 7.64-7.60 (m, 1H), 7.49-7.45 (m, 2H), 5.55-5.44 (m, 1H), 3.76-3.54 (s, 1H), 2.49-2.47 (m, 1H), 2.29-2.14 (dt, J=13.4, 6.9 Hz, 1H), 2.10 (s, 3H), 2.11-2.06 (s, 1H), 1.96-1.93 (m, 2H); $^{13}$C NMR (100 MHz, CDCl$_3$): δ192.2, 177.7, 174.0, 169.9, 135.3, 134.4, 128.9, 127.5, 73.7, 61.0, 58.2, 55.4, 33.6, 31.8, 30.4, 30.1, 29.7, 21.1, 20.8; HRMS (ESI): m/z calculated for C$_{16}$H$_{15}$NO$_5$S[M+Na]$^+$ 356.0553 found 356.0563.

Example 38

Biological Testing Results

All the synthesized analogues were subjected for biological screening against inhibition of LPS induced NO generation. The cytotoxicity effects of the synthesized analogues were also analysed and all the results were summarized in table 1 below. Compound NDS100652, NDS100653, NDS100656 showed promising inhibitory activity, selectivity index and further studies on these compounds are underway.

TABLE 1

Cytotoxicity and inhibition of compounds on LPS induced NO generation in RAW 264.7 cells

| Compound | Cytotoxicity (A) IC$_{50}$ (μM) | NO inhibition (B) IC50 (μM) | Selectivity index (A/B) |
|---|---|---|---|
| -(−)-4 | 319.2 | 121.3 | 2.631492168 |
| (−)-5 | 128 | 866.9 | 0.147653 |
| (±)-2 | 433.8 | 225.3 | 1.925433 |
| 11 | 473.7 | 318 | 1.489623 |
| 16 | 17063 | 65.2 | 261.7025 |
| 14 | 717.1 | 178.3 | 4.021873 |
| 12 | 10872.1 | 36.6 | 297.0519 |
| 33 | 12135.6 | 34.3 | 353.8076 |
| 27 | 93.07 | 30.6 | 3.041503 |
| 26 | 184.5 | 20.5 | 9 |
| 28 | 10007.6 | 19.8 | 505.4343 |
| 29 | 26.7 | 65 | 0.410769 |
| (−)-2 | 1383.9 | 140.5 | 9.849822 |
| 5 | 616.1 | 42 | 14.66905 |
| (+)-1 | 1015.6 | 71.8 | 14.14485 |
| 21 | 834.5 | 59.8 | 13.95485 |
| 23 | 210.6 | 98.3 | 2.142421 |

TABLE 1-continued

Cytotoxicity and inhibition of compounds on LPS induced NO generation in RAW 264.7 cells

| Compound | Cytotoxicity (A) IC$_{50}$ (μM) | NO inhibition (B) IC50 (μM) | Selectivity index (A/B) |
|---|---|---|---|
| 18 | 674.4 | 59.2 | 11.39189 |
| 20 | 383.6 | 389.8 | 0.984094 |
| 19 | 425.6 | 56.9 | 7.479789 |
| 10 | 773.7 | 142.8 | 5.418067 |
| 9 | 834.5 | 132 | 6.32197 |
| 8 | 856.7 | 832.8 | 1.028698 |
| 7 | 558.5 | 147.9 | 3.7762 |
| 15 | 479.4 | 72.4 | 6.621547 |
| 34 | 9076.1 | 101.4 | 89.50789 |
| 35 | 1912 | 64.3 | 29.73561 |
| 32 | 1607.3 | 68.2 | 23.56745 |
| 6 | 2914.9 | 126.8 | 22.98817 |
| (+)-4 | 216.7 | 95.9 | 2.259645 |
| 13 | 667.7 | 127.3 | 5.24509 |

Example 39

Method for Biological Assays

Cell Culture

Mouse macrophage cell line RAW 264.7 was maintained in laboratory at 37° C. in RPMI-1640 media supplemented with 10% heat-inactivated fetal bovine serum (FBS) and penicillin/streptomycin.

Cytotoxicity Assay

Viability of cultured cells was determined by (4,5-dimethylthiazol-2-yl)-2,5-diphenyltetrazolium bromide (MTT; Sigma) as described earlier (1). RAW 264.7 was seeded in triplicate at a density of 2×10$^4$ cells per well on a 96-well plate. After 12 h, cells were treated with varying concentrations (0-100 μM) of all the compounds in a serum free condition for another 24 h. MTT solution (0.5 mg/ml) was then added to each well and incubate for 4 h at 37° C. At the end of the incubation period, the medium was removed and the resulting purple formazan was solubilized with acidic isopropanol (0.1 N HCl in absolute isopropanol), and the absorbance was read at 570 nm using Biorad Microplate reader (Biorad, USA).

Nitric Oxide (NO) Measurement

Nitrite, a stable oxidized product of NO, was measured in culture supernatant using Griess reagent (Sigma Aldrich) according to a previously reported method (2). After overnight seeding in 96-well plate (2×10$^4$ cells/well), RAW 264.7 cell was treated with lipopolysaccharide (LPS; Sigma) at a concentration of 1 μg/ml along with different doses of compounds (as determined from cytotoxicity assay) in serum-free culture for 24 h. Following treatment, media was collected and centrifuged at 2,000 rpm for 5 min to remove cellular debris. 50 μl of this media was then reacted with equal volume of Griess reagent for 15 min at room temperature in dark and absorbance was taken at 540 nm using Microplate reader (Biorad, USA). Nitrite concentrations were determined using standard solutions of sodium nitrite prepared in cell culture medium.

Advantages of Invention a. Novel compounds which can be potential antivirals or anti-inflammatory agents.
b. Invention provides a synthetic route for synthesis of nitrosporeusines A (1) and B (2).

c. Process is simple and industrially scalable in view of the limited number of steps.
d. Process is cost-effective and eco-friendly.
e. Raw materials are easily available.

We claim:
1. A compound of formula (I) or a salt or a stereoisomer thereof

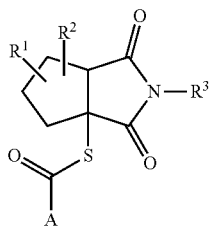

Formula (I)

wherein,
R¹ and R² are individually selected from hydrogen, alkyl, alkenyl, aryl, heteroaryl, hydroxyl, alkoxy, heteroaryloxy, carboxy, alkylcarbonyl, arylcarbonyl, alkoxycarbonyl, cyano, halo, azide, thiocyano, alkylcarbothioc or arylcarbothioc; or R¹ and R² are 3 to 8 membered carbocyclic ring which is optionally substituted or contain a 1-2 heteroatoms;
R³ is selected from hydrogen, alkyl, alkenyl, alkynyl, cycloalkyl, cylcoalkenyl, aryl, heteroaryl, hydroxyl, alkoxy, heteroaryloxy, alkylcarbonyl, arylcarbonyl, or alkoxycarbonyl;
A is selected from hydrogen, alkyl, alkenyl, alkynyl, cycloalkyl, cylcoalkenyl, unsubstituted aryl, substituted aryl wherein substitution is selected from F or Cl, heteroaryl, hydroxyl, alkoxy or aryloxy;
provided that when R² and R³ are Hydrogen, R¹ is not OH and A is not aryloxy.

2. A compound or a salt or a stereoisomer thereof, wherein the compound is selected from
a) S-((3aR*,6R*,6aS*)-6-Hydroxy-1,3-dioxohexahydrocyclopenta[c]pyrrol-3a(1H)-yl) ethanethioate (7);
b) S-((3aS*,6R*,6aR*)-6-Hydroxy-1,3-dioxohexahydrocyclopenta[c]pyrrol-3a(1H)-yl) ethanethioate (8);
c) S-((3aR*,6R*,6aS*)-6-Hydroxy-1,3-dioxohexahydrocyclopenta[c]pyrrol-3a(1H)-yl) 2-phenylethanethioate (9);
d) S-((3aS*,6R*,6aR*)-6-Hydroxy-1,3-dioxohexahydrocyclopenta[c]pyrrol-3a(1H)-yl) 2-phenylethanethioate (10);
e) S-((3aS*,6R*,6aR*)-6-Hydroxy-1,3-dioxohexahydrocyclopenta[c]pyrrol-3a(1H)-yl) 4-fluorobenzothioate (11)
f) S-((3aS*,6R*,6aR*)-6-Hydroxy-1,3-dioxohexahydrocyclopenta[c]pyrrol-3a(1H)-yl) thiophene-2-carbothioate (12)
g) S-((3aS*,6S*,6aR*)-6-Hydroxy-1,3-dioxohexahydrocyclopenta[c]pyrrol-3a(1H)-yl) 2-chlorobenzothioate (13);
h) S-((3aS*,6R*,6aR*)-6-Hydroxy-1,3-dioxohexahydrocyclopenta[c]pyrrol-3a(1H)-yl) 2-chlorobenzothioate (14);
i) S-((3aR*,6R*,6aS*)-6-Hydroxy-1,3-dioxohexahydrocyclopenta[c]pyrrol-3a(1H)-yl) benzothioate (15);
j) S-((3aS*,6R*,6aR*)-6-Hydroxy-1,3-dioxohexahydrocyclopenta[c]pyrrol-3a(1H)-yl) benzothioate (16);
k) S-((3aR*,6aS*)-1,3-Dioxohexahydrocyclopenta[c]pyrrol-3a(1H)-yl) ethanethioate (18);
l) S-((3aR*,6aS*)-1,3-Dioxohexahydrocyclopenta[c]pyrrol-3a(1H)-yl) 2-phenylethanethioate (19);
m) S-((3aR*,6aS*)-1,3-Dioxohexahydrocyclopenta[c]pyrrol-3a(1H)-yl) 4-fluorobenzothioate (20);
n) S-((3aR*,6aS*)-1,3-Dioxohexahydrocyclopenta[c]pyrrol-3a(1H)-yl) 2-chlorobenzothioate (21);
o) S,S'-((3aR*,6aR*)-1,3-Dioxohexahydrocyclopenta[c]pyrrole-3a,6(1H)-diyl) bis(4-fluorobenzothioate) (23);
p) S,S'-((3aS*,6aS*)-1,3-Dioxohexahydrocyclopenta[c]pyrrole-3a,6(1H)-diyl) dibenzothioate (25);
q) S,S'-((3 aR*,6aR*)-1,3-Dioxohexahydrocyclopenta[c]pyrrole-3a,6(1H)-diyl) diethanethioate (28);
r) (3 aS*,6aR*)-1,3-Dioxo-6a-((thiophene-2-carbonyl)thio)octahydrocyclopenta[c]pyrrol-4-yl acetate (30);
s) (3aS*,6aR*)-6a-(Acetylthio)-1,3-dioxooctahydrocyclopenta[c]pyrrol-4-yl acetate (31);
t) (3aS*,6aR*)-1,3-Dioxo-6a-((2-phenylacetyl)thio)octahydrocyclopenta[c]pyrrol-4-yl acetate (32);
u) (3aS*,6aR*)-6a-((4-Fluorobenzoyl)thio)-1,3-dioxooctahydrocyclopenta[c]pyrrol-4-yl acetate (33);
v) (3aS*,6aR*)-6a-((2-Chlorobenzoyl)thio)-1,3-dioxooctahydrocyclopenta[c]pyrrol-4-yl acetate (34);
w) (3aS*,6aR*)-6a-(Benzoylthio)-1,3-dioxooctahydrocyclopenta[c]pyrrol-4-yl acetate (35).

3. The compound as claimed in claim 1 or 2 for use in treating various viral infections.

4. A process for synthesis of compound of formula (I) or a salt or a stereoisomer thereof

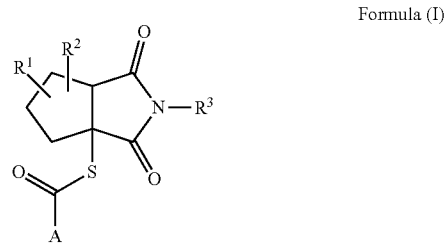

Formula (I)

wherein,
R¹ and R² are individually selected from hydrogen, alkyl, alkenyl, aryl, heteroaryl, hydroxyl, alkoxy, heteroaryloxy, carboxy, alkylcarbonyl, arylcarbonyl, alkoxycarbonyl, cyano, halo, azide, thiocyano, alkylcarbothioc or arylcarbothioc; or R¹ and R² are 3 to 8 membered carbocyclic ring which is optionally substituted or contain a 1-2 heteroatoms;
R³ is selected from hydrogen, alkyl, alkenyl, alkynyl, cycloalkyl, cylcoalkenyl, aryl, heteroaryl, hydroxyl, alkoxy, heteroaryloxy, alkylcarbonyl, arylcarbonyl, or alkoxycarbonyl;
A is selected from hydrogen, alkyl, alkenyl, alkynyl, cycloalkyl, cylcoalkenyl, unsubstituted aryl, substituted aryl wherein substitution is selected from F or Cl, heteroaryl, hydroxyl, alkoxy or aryloxy;
provided that R¹, R² and R³ are not Hydrogen at the same time; and
provided that when R² and R³ are hydrogen, R¹ is not OH and A is not aryloxy;

wherein said process comprising the step of:
i. stirring thioacid of formula (b)

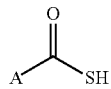

with compound of formula (a)

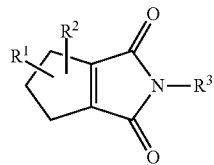

in solvent at a temperature in the range of 25° C. to 100° C. for period in the range of 2 to 15 hrs followed by extraction to afford compound of formula (I).

5. The process as claimed in claim 4, wherein said compound of formula (a) is selected from 4-hydroxy-5,6-dihydrocyclopenta[c]pyrrole-1,3(2H,4H)-dione (4), and 4-bromo-5,6-dihydrocyclopenta[c]pyrrole-1,3(2H,4H)-dione.

6. The process as claimed in claim 4, wherein said compound of formula (b) is selected from ethanethioic S-acid, 2-chlorobenzothioic S-acid, 4-fluorobenzothioic S-acid, benzothioic S-acid, and thiophene-2-carbothioic S-acid.

7. The process as claimed in claim 4, wherein said solvent is selected from hydrocarbon solvents, water, alcohols, ethers, esters, cyclic ethers and nitriles or a combination thereof.

8. A pharmaceutical composition useful for treating various viral infections comprising a compound of formula (I) as claimed in claim 1 and at least one pharmaceutically acceptable carrier.

* * * * *